United States Patent [19]

Benedix et al.

[11] Patent Number: 5,446,196
[45] Date of Patent: Aug. 29, 1995

[54] PROCESS FOR THE PRODUCTION OF ISOCYANATES AND FOR THE CONTINUOUS WORKING-UP OF THE RESIDUE

[75] Inventors: Hermann-Josef Benedix; Werner Motika, both of Marne, Germany

[73] Assignee: Bayer Aktiengesellschaft, Leverkusen, Germany

[21] Appl. No.: 247,786

[22] Filed: May 23, 1994

[30] Foreign Application Priority Data

May 27, 1993 [DE] Germany .................. 43 17 669.0

[51] Int. Cl.⁶ .............................................. C07C 71/00
[52] U.S. Cl. .............................................. 560/352
[58] Field of Search .................................... 560/352

[56] References Cited

U.S. PATENT DOCUMENTS

| | | | |
|---|---|---|---|
| 2,889,257 | 6/1959 | Griffin et al. | 202/52 |
| 3,457,291 | 7/1969 | Baylor | 260/453 |
| 3,687,422 | 8/1972 | List | 259/104 |
| 3,971,793 | 7/1976 | Fauran et al. | 260/293.58 |
| 4,216,063 | 8/1980 | Ailloud et al. | 203/91 |
| 4,289,589 | 9/1981 | Koehler et al. | 203/49 |
| 5,043,470 | 8/1991 | Dibase et al. | 560/352 |

FOREIGN PATENT DOCUMENTS 269218 6/1988 European Pat. Off. .

OTHER PUBLICATIONS

Ullmanns Encyklopädie der technischen Chemie, Fourth Edition, vol. 13, pp. 347–357, Verlag Chemie GmbH, D-69469 Weinheim, 1977.

Primary Examiner—José G. Dees
Assistant Examiner—Samuel Barts
Attorney, Agent, or Firm—Joseph C. Gil; Lyndanne M. Whalen

[57] ABSTRACT

Pure isocyanate is recovered from an isocyanate-containing residue of a phosgene/amine reaction mixture by continuously feeding such residue and a high boiling hydrocarbon such as bitumen to a heated vacuum drier with a horizontal shaft. The contents of the drier are subjected to temperatures of from about 160° to about 280° C. and pressures of from about 2 to about 50 mbar. Pure isocyanate and a pourable, non-dusting, granular material are recovered.

9 Claims, 1 Drawing Sheet

PROCESS FOR THE PRODUCTION OF ISOCYANATES AND FOR THE CONTINUOUS WORKING-UP OF THE RESIDUE

BACKGROUND OF THE INVENTION

The present invention relates to a process for the production of pure, distilled isocyanates and to a multi-stage distillation process for working-up the residue of this production process.

Processes for the large-scale production of distilled isocyanates by reacting an amine with phosgene in a solvent are known. Such processes are described in detail in the literature (See, e.g., Ullmanns Encyklopädie der technischen Chemie Fourth Edition, Volume 13, pages 347–357, Verlag Chemie GmbH, D-69469 Weinheim, 1977). It is also known that a by-product stream is generated during the production of pure isocyanates by such distillation processes. This by-product stream has to be disposed of as a residue after free isocyanate has been separated as much as possible by distillation. In laboratory tests, it is possible to distill off significant additional amounts of free isocyanate from this residue stream. However, the remaining residue becomes a hard cross-linked mass which cannot be handled in a commercial process. Therefore, about 20–40% of free isocyanate is left in the residue stream from the commercial process to ensure that the residue stream can be handled. Consequently, valuable material is lost and the amount of waste to be disposed of is greater.

Processes for recovering additional free isocyanate from the residue are known. For example, GB 1,408,745 describes an extraction process for recovering the free isocyanate. EP 269,218 describes a process in which the residue stream is heated using a bath of molten metal or metal salts. A distillation process performed on isocyanate-containing residue in a fluidized bed is described in DE 2,915,830. Each of these processes requires costly apparatus and/or auxiliary process materials. Auxiliary process materials such as metals or metal salts, for example, make subsequent disposal considerably more difficult.

SUMMARY OF THE INVENTION

It is an object of the present invention to provide a technically simple and reliable process for recovering isocyanate from the residues of the production process in greater amounts than the known processes.

It is another object of the present invention to provide a process for recovering isocyanate from the residues of the production process which avoids the ecological and economical complications of the known recovery processes.

It is also an object of the present invention to provide a process for recovering isocyanate from the residues of the production process in which the final residue, which cannot be worked up further, can be disposed of simply and without causing environmental contamination.

It is another object of the present invention to provide an apparatus for carrying out the inventive process.

These and other objects which will be apparent to those skilled in the art are accomplished by continuously feeding the isocyanate-containing residue from the isocyanate production process together with from about 2 to about 50% by weight of a high boiling hydrocarbon which is inert under the process conditions (e.g., a bitumen) to a heated, product-agitating vacuum drier with a horizontal shaft and continuously distilling off isocyanate at a temperature of from about 160° to about 280° C. and at a pressure of from about 2 to about 50 mbar. The residue which is continuously discharged is a pourable, non-dusting, granular material. This recovery process is carried out in a continuously operating, heated, product-agitating vacuum drier with a horizontal shaft and a plurality of product inlets distributed over the length of the drier.

BRIEF DESCRIPTION OF THE DRAWING

The FIGURE illustrates an apparatus useful in carrying out the process of the present invention.

DETAILED DESCRIPTION OF THE PRESENT INVENTION

Figure 1:
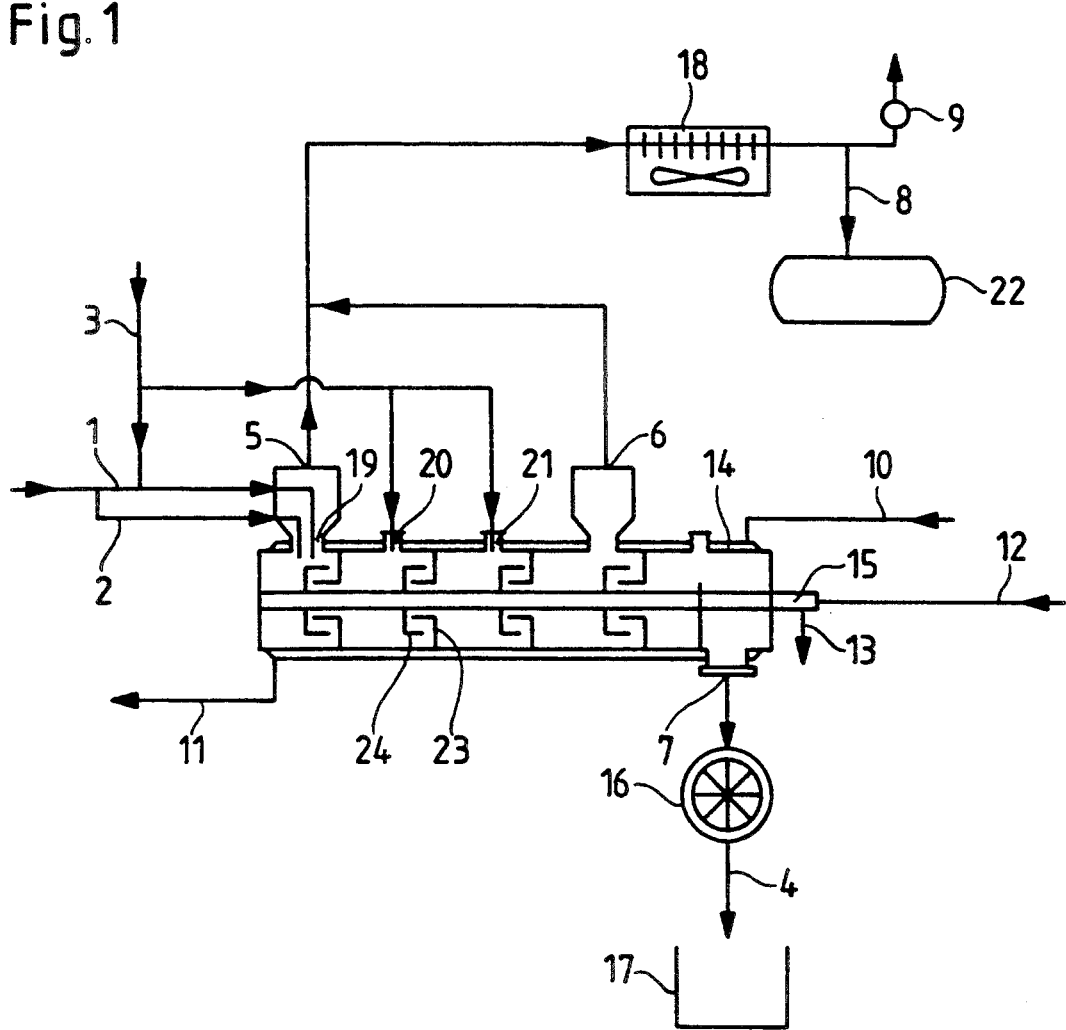

The present invention relates to a process for the production of pure, distilled isocyanates by the reaction of the corresponding amines with phosgene in a suitable solvent and multi-stage distillative work-up of the isocyanate solution obtained to recover pure isocyanate, pure solvent and a residue. The residue obtained from this distillation process and from about 2 to about 50 weight % of a high-boiling hydrocarbon (preferably a bitumen) which is inert under the distillation conditions, are continuously fed to a heated, product-agitating vacuum drier with a horizontal shaft. The fraction of isocyanate still present is continuously distilled off from the residue at temperatures of from about 160° to about 280° C. and pressures from about 2 to about 50 mbar. The remaining residue is continuously discharged as a pourable, non-dusting, granular material, which is optionally cooled and optionally incinerated after grinding.

Additional isocyanate can surprisingly be distilled from the residue with the high-boiling hydrocarbon or hydrocarbon mixtures, preferably a bitumen, under the appropriate distillation conditions for a given isocyanate. In the course of this procedure, a granular, free-flowing mass which is practically free from isocyanate is recovered from the mixture of high-boiling hydrocarbons and the non-distillable polymer fraction of the residue. The recovered residue may be cooled before intermediate storage or further processing.

A major advantage of the recovery process of the present invention is that chlorine-containing impurities present are removed to a very great extent during the working-up of the residue. These chlorine-containing materials may be re-used.

The process of the present invention can be used to recover a number of different isocyanates. Examples of specific isocyanates which may be recovered in accordance with the present invention include: toluene diisocyanate, 1,6-hexanediisocyanate, 1-isocyanato-3,3,5-trimethyl-5-isocyanato-methylcyclohexane, naphthalene 1,5-diisocyanate, and diisocyanato-diphenylmethane.

The residue formed during distillation of the amine/phosgene reaction mixture normally contains from about 20 to about 80 weight % of free isocyanate (preferably from about 40 to about 60 weight % of free isocyanate) in addition to polymeric by-products. Almost all of this isocyanate is distilled off and recovered in the process of the present invention.

Physiologically active vapor-phase components can no longer be detected over the cooled, discharged residue remaining after carrying out the process of the present invention because almost all of the isocyanate is recovered.

In the practice of the present invention, the isocyanate-containing residue may preferably be fed to the drier separately from the hydrocarbons in a plurality of partial streams.

Part of the isocyanate-containing residue is most preferably mixed with the hydrocarbon and fed to the drier. The remainder of the residue may then be fed to the drier in one or more partial streams.

The discharged, granular residue is preferably cooled before it is disposed of, e.g. by incineration.

The present invention also relates to the use of an apparatus comprising a continuously operating, heated, product-agitating vacuum drier with a horizontal shaft and a plurality of product inlets distributed over the length of the drier for the removal of isocyanates from the residue being treated (i.e., the distillation residue of the phosgene/amine reaction mixture).

A continuously operating contact drier which has a double shell for heating, has a horizontal shaft which agitates the product and is heated is used as the drier in the practice of the present invention. The apparatus used in the process of the present invention will preferably have a plurality of nozzles for product admission, one nozzle for product discharge, and vapor discharge nozzles of large dimensions for the isocyanate and solvent which are separated from the residue during the distillation. Other auxiliary devices may, of course, be included in the apparatus for carrying out the process of the present invention.

It is preferred that an apparatus with devices for cleaning both the shaft and the drier housing be used. In a particularly preferred embodiment of the present invention, the cleaning device for the shaft is made up of counter-hooks attached to the housing. Both single-shaft driers and double-shaft or screw feed apparatuses may be used.

Condensate formed from vapors generated during the process of the present invention (e.g., in a vapor offtake system) may be used to remove dust deposits such as those which may be formed on the walls of the apparatus at the point where vapors are removed from the system (e.g., the vapor offtake system). These condensates are separately discharged.

In the process of the present invention, the reactor is operated at a temperature of from about 160° to about 280° C. (preferably from about 200° to about 250° C.), under a pressure of from about 2 to about 50 mbar (preferably from about 10 to about 20 mbar) at a throughput of up to 250 kg/hour per $m^2$ of heating surface. The continuous distillation is preferably conducted in a product-agitating drier with a horizontal shaft, to which a condensation system is attached. Distillation is carried out in the presence of one or more hydrocarbons, which are admixed in an amount of from about 2 to about 50 weight %, preferably from about 10 to about 20 weight %, based on the weight of the residue being treated. Pure hydrocarbons and also industrial mixtures, preferably bitumens, which have a boiling point which is different from the boiling point of the isocyanate being recovered by at least 150° C. at 15 mbar, may be used as the high boiling hydrocarbon in the process of the present invention. Asphalts and bitumens, such as those which occur industrially as by-products in the refining of crude oil are particularly preferred from an economic point of view. Bitumens, particularly those of type B 80, B 80 E, B 300 or B 300 E (characterization according to DIN 52 010) are most preferred.

The residue of the process of the present invention (discharged e.g., via a vacuum lock) may be continuously cooled via a cooled surface (e.g., the surface of a feed screw).

Having thus described our invention, the following Examples are given as being illustrative thereof. All percentages given in these Examples are percentages by weight, unless otherwise indicated.

EXAMPLES

EXAMPLE 1

An apparatus corresponding to that shown in the Figure was used. With reference to the Figure, this apparatus was made up of a horizonal cylindrical housing 14 with an inside diameter of 280 mm and a length of 1700 mm. Housing 14 had three product (i.e., isocyanate-containing residue) admission nozzles 19, 20, and 21. Housing 14 also had one product discharge nozzle 7 and two gas discharge nozzles 5 and 6. Product agitation and axial product transport were achieved by using a shaft 15 provided with mixing bars 24. Shaft 15 was kept substantially free from caked product deposits by means of counter-hooks 23 which were attached to the housing 14.

Housing 14 and shaft 15 were heated by heat-transfer oil via admission nozzles 10 and 12 and discharge nozzles 11 and 13.

Isocyanate-containing residue was fed to admission nozzles 19, 20 and 21. A vacuum-tight cellular wheel lock 16 conveyed the residue from which isocyanate had been recovered in accordance with the present invention into collection vessel 17. Wheel lock 16 was positioned on product discharge nozzle 7. Vapor offtake nozzles 5 and 6 were connected to air-cooled condenser 18 which was attached to vacuum pump 9. Condensate 8 which formed was fed to vessel 22.

The isocyanate-containing residue to be treated in accordance with the process of the present invention was a product from the industrial production of toluene diisocyanate which was a mixture of 2,4 -and 2,6-isomers in which 80% was the 2,4-isomer. This isocyanate-containing residue was composed of 67.4 weight % isomeric mixture of toluene diisocyanate, 29.1 weight % of polymeric residue and 3.5 weight % solvent.

The isocyanate-containing residue to be treated (stream 3 in the Figure) was admixed with bitumen of the type B 80 (stream 1 in the Figure) before being introduced into housing 14. The isocyanate-containing residue (stream 3) was continuously fed at a rate of 57 kg/hour. The bitumen (stream 1) was fed at a rate of 8.3.kg/hour. This admixture with a temperature of 140° C. was continuously fed to housing 14 at admission nozzle 19 into the contact drier (i.e., heated housing 14 and shaft 15). Housing 14 and shaft 15 were heated to a temperature of 240° C. and evacuated to a pressure of 12 mbar. Heat was supplied to the isocyanate-containing residue/bitumen stream by rotating shaft 15 via the heated surfaces of shaft 15 and housing 14. The toluene diisocyanate and solvent contained in the feed material were evaporated off and fed to air condenser 18. A distillate yield of 40.2 kg/hour (stream 8) was obtained. This distillate was made up of 38.2 kg of toluene diisocyanate and 2.0 kg of solvent. 25.1 kg/hour (stream 4) of a pourable, odorless, non-dusting granular material with a non-distillable residual toluene diisocyanate content of <1% was discharged via cellular wheel lock 16 into collection vessel 17.

EXAMPLE 2

Example 1 was repeated with the exception that the amount of bitumen was different and the residue/bitumen mixture was distributed over three admission nozzles. The same amount of isocyanate-containing residue having the same composition as that used in Example 1 was fed into housing 14. The amount of bitumen of type 80 B was reduced from 8.3 kg/hour to 3.0 kg/hour. The residue/bitumen mixture was distributed over admission nozzles 19, 20 and 21. 10.3 kg/hour of isocyanate-containing residue with which 3.0 kg/hour bitumen had been admixed were fed into housing 14 via admission nozzle 19. Half of the remaining amount of 46.7 kg/hour of isocyanate-containing residue was fed into housing 14 via each of admission nozzles 20 and 21.

The amount and composition of the distillate obtained and the properties of the residue formed were comparable with those of Example 1.

EXAMPLE 3

Example 2 was repeated, with the same amount of product being fed into the drier, the same product composition, and the same amount of bitumen of type B 80 with the exception that the amount of bitumen (stream 2) was heated to 230° C. and was fed into housing 14 via admission nozzle 19 separately from the isocyanate-containing residue (stream 3).

The amount and composition of the distillate obtained and the properties of the residue formed were comparable with those of Example 1.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for recovering a pure isocyanate from an isocyanate-containing residue of a phosgene/amine reaction mixture comprising a) distilling the reaction mixture to separate it into an isocyanate fraction, a solvent fraction and an isocyanate-containing residue,
   b) continuously feeding
      (1) the isocyanate-containing residue obtained in a) and
      (2) one or more high-boiling hydrocarbons which are inert with respect to the isocyanate-containing residue under distillation conditions in an amount of from about 2 to about 50 weight %, based on the total weight of (1) plus (2)
      to a heated, product-agitating vacuum drier with a horizontal shaft,
   c) continuously distilling the mixture of b) at a temperature of from about 160° to about 280° C. and a pressure of from about 2 to about 50 mbar to remove isocyanate present in that mixture, and
   d) recovering as residue from distillation c) a pourable, non-dusting, granular material.

2. The process of claim 1 in which the high-boiling hydrocarbon is a bitumen.

3. The process of claim 1 in which the granular residue recovered in d) is cooled.

4. The process of claim 1 in which the granular residue recovered in d) is ground and incinerated.

5. The process of claim 1 in which that the isocyanate-containing residue (1) is fed separately from the hydrocarbon (2) to the drier in step b).

6. The process of claim 5 in which the isocyanate-containing residue (1) is fed to the drier in a plurality of partial streams in step b).

7. The process of claim 1 in which a portion of the isocyanate-containing residue (1) is mixed with the hydrocarbon (2) before being fed to the drier in step b) and the remaining portion of the isocyanate-containing residue (1) is fed to the drier separately in step b).

8. The process of claim 7 in which the isocyanate-containing residue (1) which is not mixed with the hydrocarbon is fed to the drier in more than one stream in step b).

9. The process of claim 1 in which the drier used in step b) is a continuously operating, heated, product-agitating vacuum drier with a horizontal shaft and a plurality of product inlets distributed over the length of the drier.

* * * * *